(12) United States Patent
Gore et al.

(10) Patent No.: US 8,846,916 B2
(45) Date of Patent: Sep. 30, 2014

(54) SITAGLIPTIN SYNTHESIS

(75) Inventors: Vinayak Govind Gore, Maharashtra (IN); Maheshkumar Gadakar, Maharashtra (IN); Priyanka Bhosle, Maharashtra (IN); Suresh Shinde, Maharashtra (IN)

(73) Assignee: Generics [UK] Limited, Hertfordshire (GB)

( * ) Notice: Subject to any disclaimer, the term of this patent is extended or adjusted under 35 U.S.C. 154(b) by 0 days.

(21) Appl. No.: 13/265,087

(22) PCT Filed: May 10, 2010

(86) PCT No.: PCT/GB2010/050760
§ 371 (c)(1),
(2), (4) Date: Jan. 18, 2012

(87) PCT Pub. No.: WO2010/131025
PCT Pub. Date: Nov. 18, 2010

(65) Prior Publication Data
US 2012/0108598 A1  May 3, 2012

(30) Foreign Application Priority Data
May 11, 2009 (IN) .............................. 722/KOL/2009

(51) Int. Cl.
C07D 471/04 (2006.01)
C07C 229/34 (2006.01)
C07D 487/04 (2006.01)

(52) U.S. Cl.
CPC ........... *C07D 487/04* (2013.01); *C07B 2200/07* (2013.01); *C07C 229/34* (2013.01)
USPC ...................................................... 544/350

(58) Field of Classification Search
USPC ...................................................... 544/350
See application file for complete search history.

(56) References Cited

U.S. PATENT DOCUMENTS

| 6,699,871 B2 | 3/2004 | Edmondson et al. |
| 2005/0032804 A1 | 2/2005 | Cypes et al. |

(Continued)

FOREIGN PATENT DOCUMENTS

| CN | 101903390 | 12/2010 |
| CN | 101928289 | 12/2010 |

(Continued)

OTHER PUBLICATIONS

Zeng, 2009, Chinese Chemical Letters, vol. 20, p. 1397-1399.*

(Continued)

*Primary Examiner* — Rebecca Anderson
*Assistant Examiner* — Karen Cheng
(74) *Attorney, Agent, or Firm* — Fulbright & Jaworski LLP; Scott D. Rothenberger

(57) ABSTRACT

The present invention relates to novel processes for the preparation of enantiomerically enriched β-amino acid derivatives such as β-amino esters useful for the synthesis of enantiomerically enriched biologically active molecules such as sitagliptin. The key step involves the resolution of the racemate with mandelic acid.

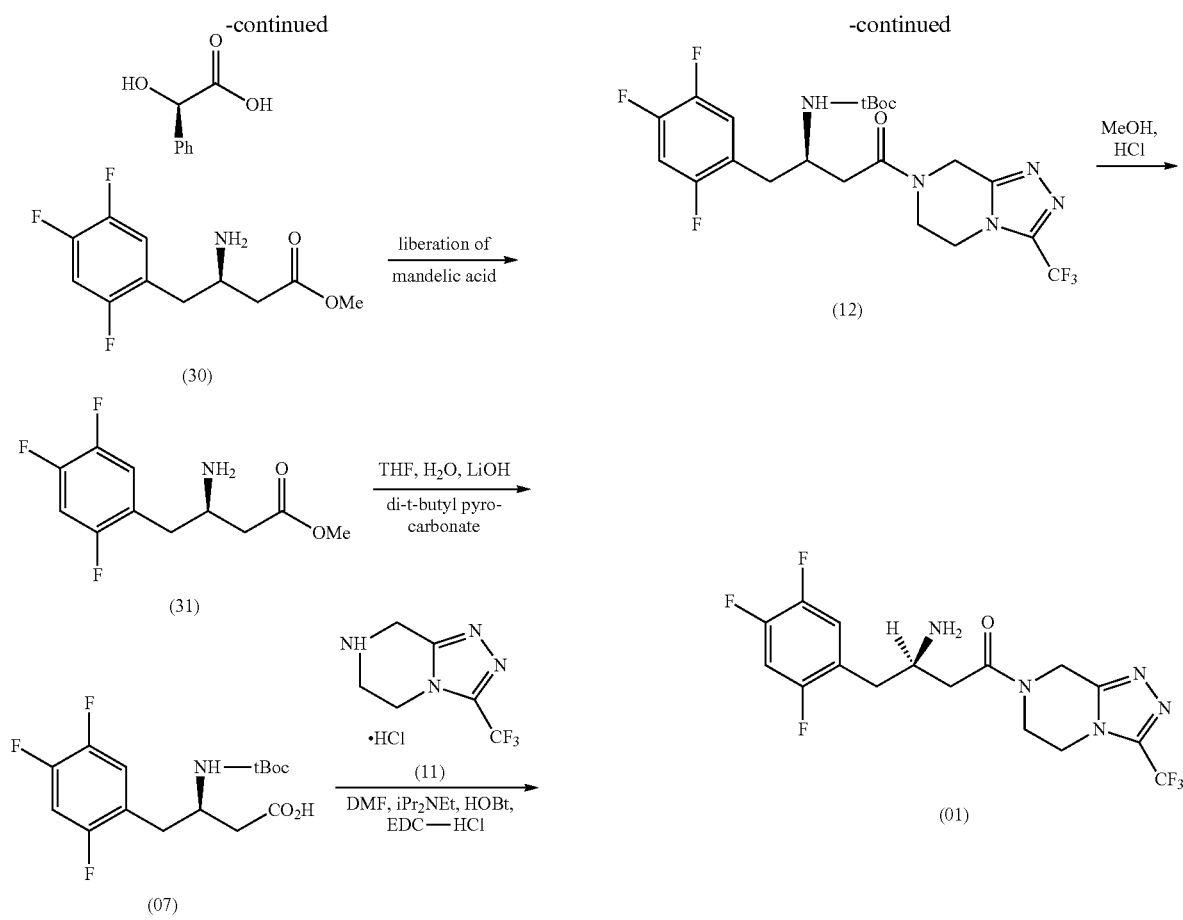

(56) References Cited

U.S. PATENT DOCUMENTS

Figure 1:
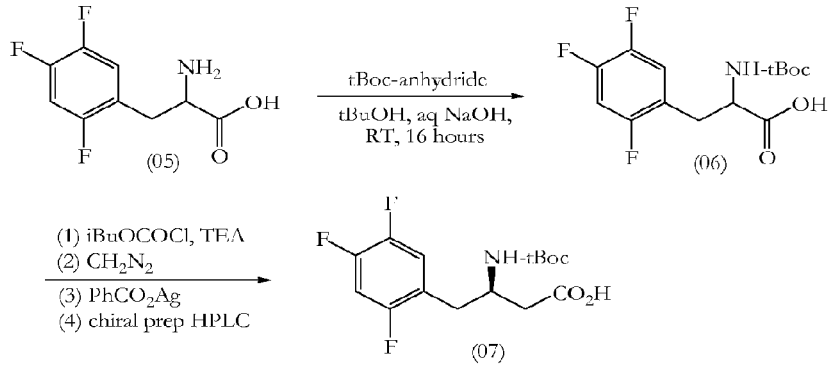
Figure 1:
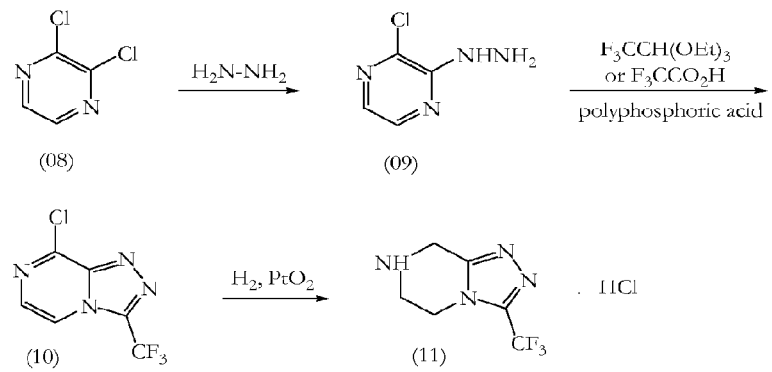
Figure 1:
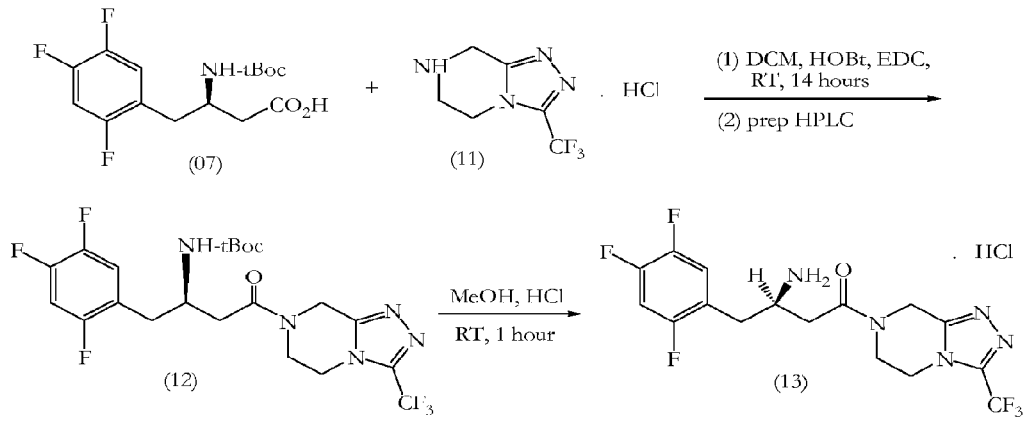
Figure 2:
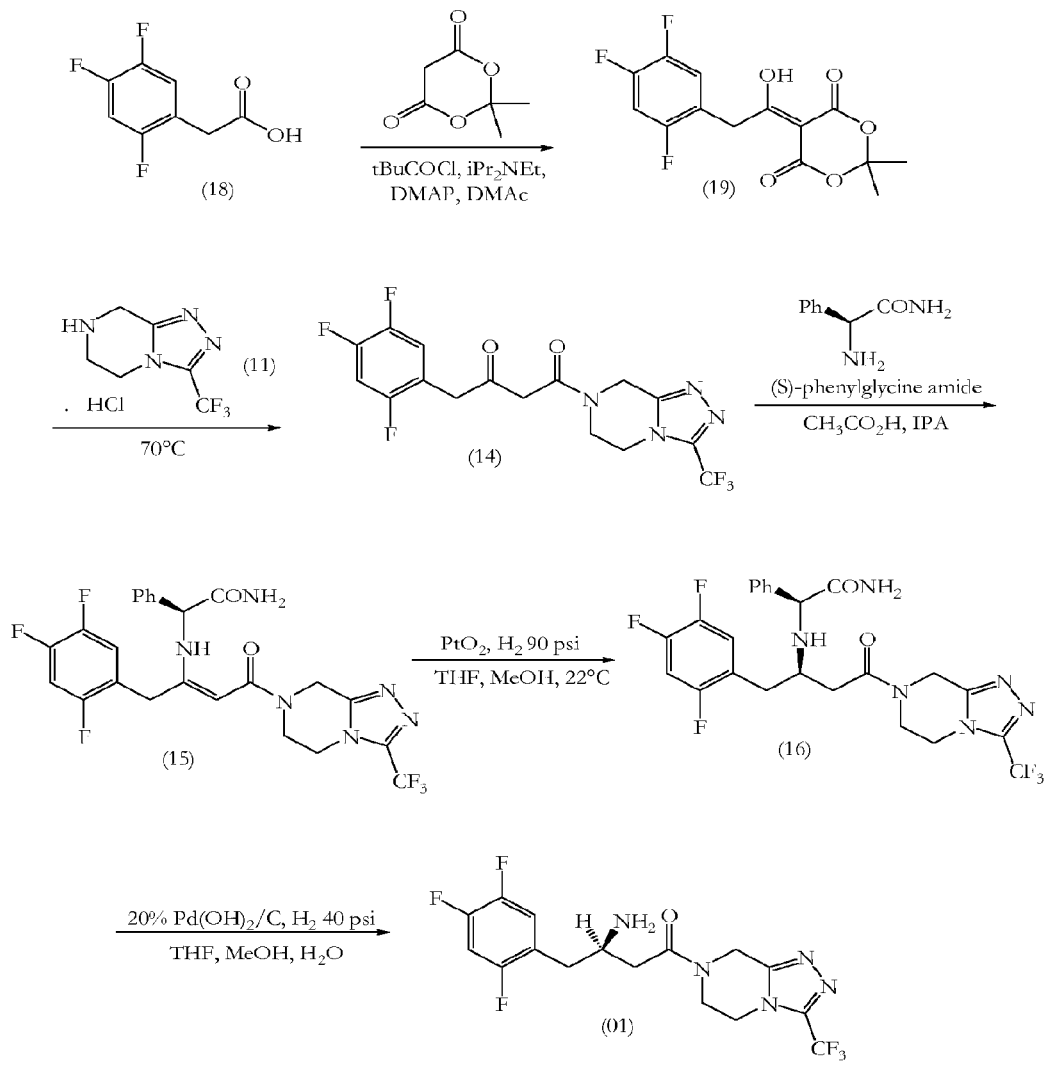
Figure 3:
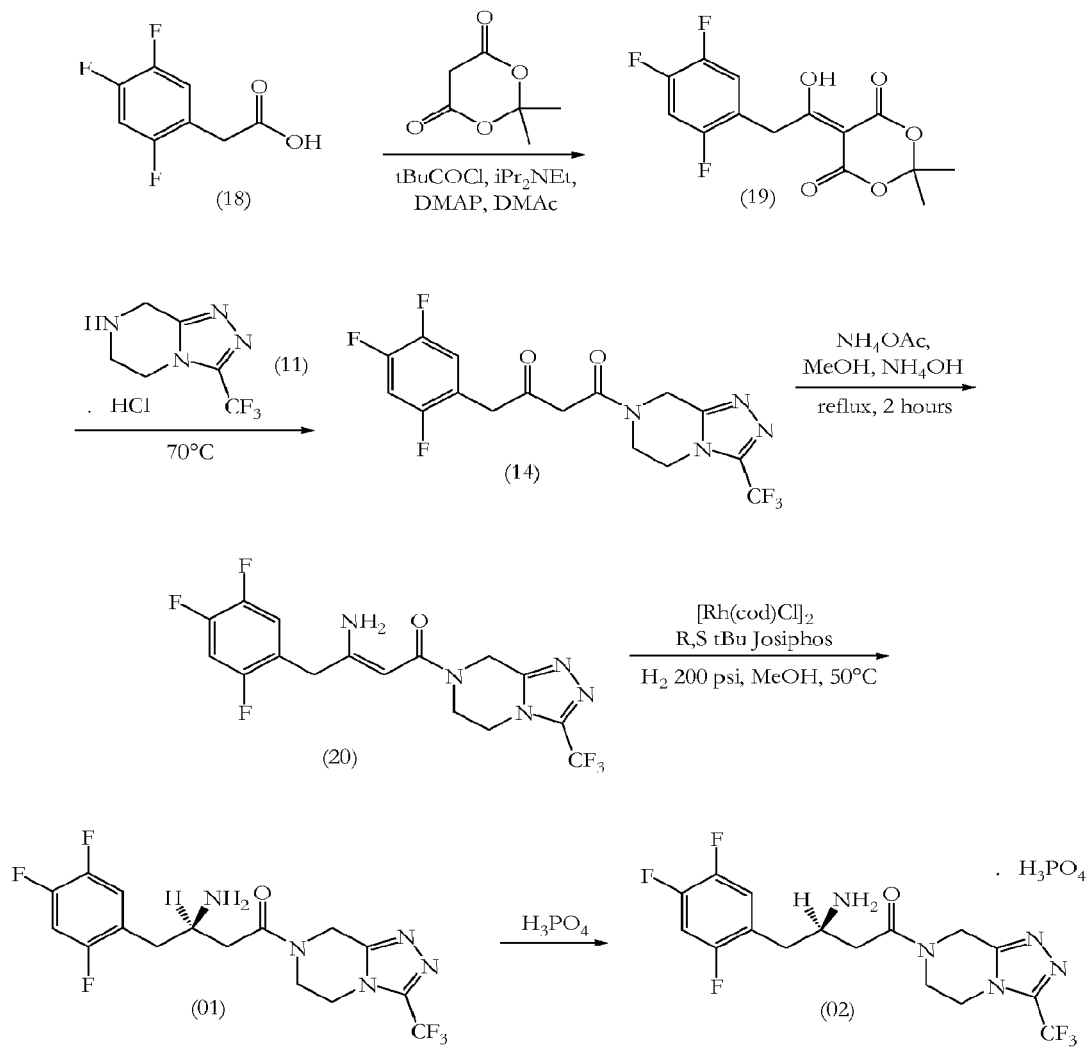
Figure 4:
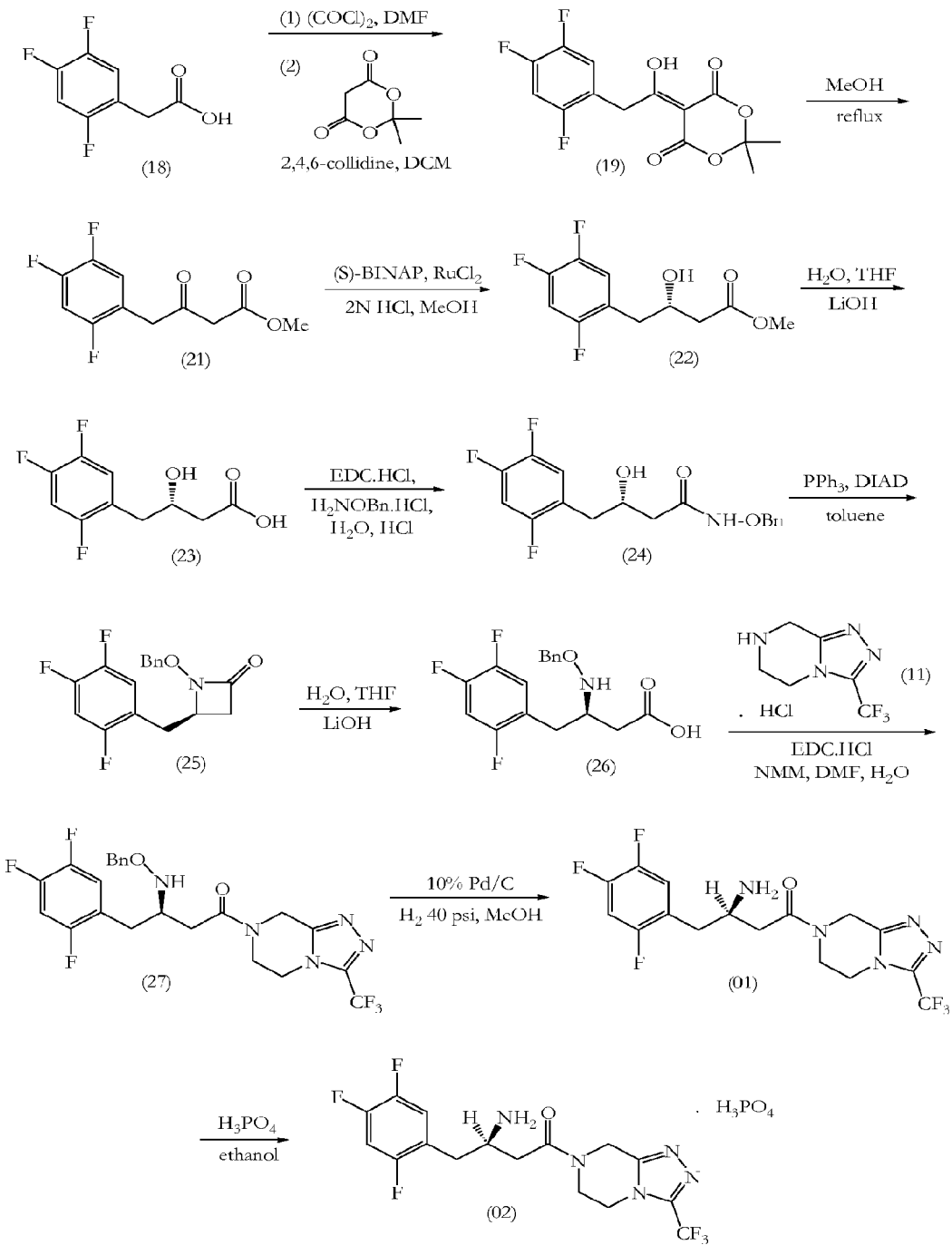

| | | |
|---|---|---|
| 2006/0194977 A1 | 8/2006 | Xiao et al. |
| 2006/0287528 A1 | 12/2006 | Wenslow et al. |
| 2007/0021430 A1 | 1/2007 | Chen et al. |
| 2007/0281941 A1 | 12/2007 | Ferlita et al. |
| 2009/0247532 A1 | 10/2009 | Huang et al. |

FOREIGN PATENT DOCUMENTS

| | | |
|---|---|---|
| WO | WO 03/004498 | 1/2003 |
| WO | WO 2004/085661 | 10/2004 |
| WO | WO 2004/087650 | 10/2004 |
| WO | WO 2005/003135 | 1/2005 |
| WO | WO 2005/020920 | 3/2005 |
| WO | WO 2005/030127 | 4/2005 |
| WO | WO 2006/065826 | 6/2006 |
| WO | WO 2009/064476 | 5/2009 |
| WO | WO 2009/084024 | 7/2009 |
| WO | WO 2009/085990 | 7/2009 |
| WO | WO 2010/032264 | 3/2010 |
| WO | WO 2010/131035 | 11/2010 |

OTHER PUBLICATIONS

"Analogue", Nov. 6, 2013, retrieved from http://www.thefreedictionary.com/p/analogue.*

International Search Report PCT/GB2010/050760 dated Aug. 13, 2010 (5 pgs.).

Kubryk M. et al., "Application of the asymmetric hydrogenation of enamines to the preparation of a beta-amino acid pharmacophore", Tetrahedron Asymmetry, Pergamon Press Ltd., Oxford, GB LNKD-DOI:10.1016/J. Tetasy, 2005.12.016, vol. 17, No. 2, Jan. 23, 2006, pp. 205-209.

Kubryk, et al., "Application of the asymmetric hydrogenation of enamines to the preparation of a beta-amino acid pharmacophore", Tetrahedron Asymmetry, No. 17, 2006, pp. 205-209.

* cited by examiner

Preparation of intermediate (07)

Preparation of intermediate (11)

Coupling of intermediate (07) and intermediate (11)

Scheme 1

Scheme 2

Scheme 3

Scheme 4

Scheme 5

SITAGLIPTIN SYNTHESIS

CROSS-REFERENCE TO RELATED APPLICATIONS(S)

This is a Section 371 National Stage Application of International No. PCT/GB2010/050760, filed on 10 May 2010, and published as WO 2010/131025 A1 on 18 Nov. 2010, which claims priority from IN Patent Application No. 722/KOL/2009, filed 11 May 2009, the contents of which are incorporated herein in their entirety for all purposes.

FIELD OF THE INVENTION

The present invention relates to novel processes for the preparation of enantiomerically enriched β-amino acid derivatives such as β-amino esters useful for the synthesis of enantiomerically enriched biologically active molecules such as sitagliptin (01) and sitagliptin dihydrogen phosphate (02). The present invention further relates to pharmaceutical compositions comprising such biologically active molecules and to the use of such compositions.

BACKGROUND OF THE INVENTION

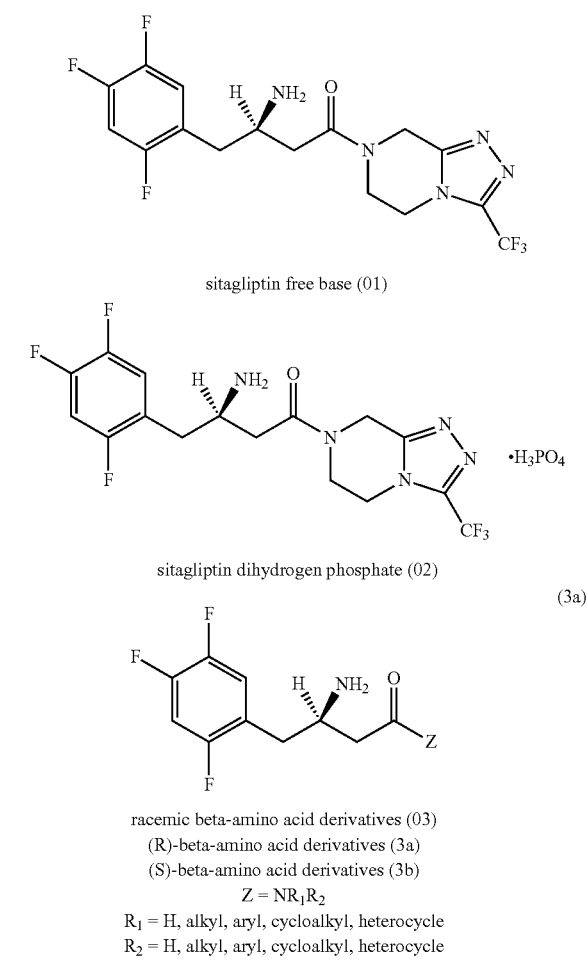

sitagliptin free base (01)

sitagliptin dihydrogen phosphate (02)

(3a)

racemic beta-amino acid derivatives (03)
(R)-beta-amino acid derivatives (3a)
(S)-beta-amino acid derivatives (3b)
Z = NR₁R₂
R₁ = H, alkyl, aryl, cycloalkyl, heterocycle
R₂ = H, alkyl, aryl, cycloalkyl, heterocycle

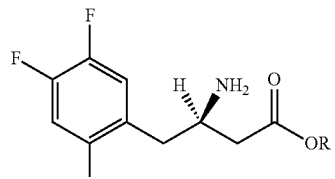

(4a)

racemic beta-amino esters (04)
(R)-beta-amino esters (4a)
(S)-beta-amino esters (4b)
R = alkyl, alkenyl, alkynyl, aryl, arylalkyl Sitagliptin dihydrogen phosphate (02), chemically named as (2R)-4-oxo-4-[3-(trifluoromethyl)-5,6-dihydro[1,2,4]triazolo[4,3-a]pyrazin-7(8H)-yl]-1-(2,4,5-trifluorophenyl)butan-2-amine dihydrogen phosphate, is an oral antihyperglycemic of the dipeptidyl peptidase-IV (DPP-IV) inhibitor class. Inhibition of DPP-IV, an enzyme that inactivates both glucose-dependent insulinotropic peptide (GIP) and glucagon-like peptide 1 (GLP-1), represents a recent approach to the treatment and prevention of type-2 diabetes, also known as non-insulin dependent diabetes mellitus (NIDDM). Sitagliptin also has an effect on appetite as it slows down gastric motility and induces a feeling of satiety. This reduction of appetite can help patients to lose weight which is also a useful effect in patients with diabetes.

Several processes have been disclosed in the prior art for the preparation of sitagliptin and its analogues. The process disclosed in patent U.S. Pat. No. 6,699,871, outlined in Scheme 1, involves the preparation of the intermediates (3R)-3-[N-(tert-butoxycarbonyl)amino]-4-(2,4,5-trifluorophenyl) butanoic acid (07) and 3-trifluoromethyl-5,6,7,8-tetrahydro-[1,2,4]triazolo[4,3-a]pyrazine hydrochloride (11) followed by their coupling to afford Boc-protected sitagliptin base (12), which was deprotected using methanolic hydrochloride to obtain sitagliptin hydrochloride (13).

However, the process disclosed in patent U.S. Pat. No. 6,699,871 suffers from the major disadvantage that the purification and synthesis of intermediates (07) and (12) require the use of preparative chiral HPLC and preparative HPLC respectively, which are very expensive and inconvenient techniques on an industrial scale. In addition, the process involves the use of the toxic and harmful reagent diazomethane.

In another prior art process, disclosed in patent application WO 2004/085661, sitagliptin free base (01) was synthesized by the process illustrated in Scheme 2, which involves synthesis of keto-amide (14) from Meldrum's adduct (19) and 3-trifluoromethyl-5,6,7,8-tetrahydro[1,2,4]triazolo[4,3-a] pyrazine hydrochloride (11). The intermediate (14) was further treated with (S)-phenylglycine amide in isopropanol and acetic acid to obtain amide (15), which was further converted into the amide (16) by asymmetric hydrogenation at 90 psi and 22° C. for 24 hours in the presence of PtO₂ as catalyst. The intermediate (16) was converted into sitagliptin free base (01) by a debenzylation reaction carried out at 40 psi at 50° C. in the presence of 20% palladium hydroxide on carbon.

However, the processes disclosed in patent application WO 2004/085661 are not suitable for industrial production as they involve expensive agents like PtO₂ and palladium hydroxide and require reaction at high pressure for more than 24 hours.

In another prior art process, disclosed in patent application US 2006/194977, sitagliptin dihydrogen phosphate salt (02) was prepared by the process outlined in Scheme 3. Intermediate (14), prepared by reaction of Meldrum's adduct (19) and 3-trifluoromethyl-5,6,7,8-tetrahydro[1,2,4]triazolo[4,3-a]pyrazine hydrochloride (11), was further converted into enamine (20) by use of ammonium acetate in methanol. The enamine (20) was further converted into enantiomerically enriched sitagliptin free base (01) by asymmetric reduction using Josiphos catalyst and chloro(1,5-cyclooctadiene)rhodium (I) dimer. The asymmetric synthesis involves hydrogenation of the enamine (20) at 200 psi at 50° C. for 13 hours to obtain enantiomerically enriched sitagliptin free base (01).

However, this process is not suitable for industrial production as it involves a very expensive chiral catalyst and requires reaction at high pressure for more than 10 hours.

A further process for the synthesis of sitagliptin free base (01) is disclosed in patent application WO 2004/087650. The process, outlined in Scheme 4, involves the synthesis of methyl 4-(2,4,5-trifluorophenyl)acetoacetate (21) by refluxing Meldrum's adduct (19) in methanol. The β-ketoester (21) formed was further subjected to asymmetric hydrogenation using ruthenium dichloride and (S)-BINAP to obtain (3S)-4-(2,4,5,-trifluorophenyl)-3-hydroxybutanoic acid (23), which was further converted into the oxazetidine (25) via hydroxy intermediate (24). The oxazetidine (25) was converted into (3R)-3-[(benzyloxy)amino]-4-(2,4,5-trifluorophenyl)butanoic acid (26) and this was further converted into enantiomerically enriched sitagliptin free base (01) and sitagliptin dihydrogen phosphate (02).

However, the processes disclosed in patent application WO 2004/087650 are not suitable for industrial production as they involve a very expensive chiral catalyst and require reaction at high pressure.

As discussed above, the prior art teaches a variety of asymmetric syntheses to prepare enantiomerically enriched β-amino acids and their derivatives in the preparation of sitagliptin. The prior art also illustrates the importance of β-amino acid derivatives, in particular β-amino esters and amides, as key intermediates for the synthesis of sitagliptin free base (01) and sitagliptin dihydrogen phosphate (02). However, as discussed, the prior art processes suffer from various disadvantages with respect to commercial production.

In view of the importance of sitagliptin free base (01) and its dihydrogen phosphate salt (02) for anti-diabetic treatment, there is a great need for a simple, convenient, inexpensive and commercially viable process for the synthesis of sitagliptin with a commercially acceptable yield and purity.

Optical resolution is a particularly convenient technique for the commercial production of chiral molecules as the technique eliminates the problems associated with asymmetric synthesis. Surprisingly, the resolution of racemic β-amino acids or derivatives to obtain enantiomerically enriched β-amino acids or derivatives and their subsequent conversion into enantiomerically enriched sitagliptin free base (01) and its dihydrogen phosphate salt (02) has not been reported in any of the prior art.

Surprisingly, the present inventors have developed a method of resolution of racemic β-amino acid derivatives, in particular β-amino esters, to obtain enantiomerically enriched β-amino acid derivatives which are extremely suitable for the synthesis of enantiomerically pure sitagliptin and salts thereof.

OBJECTS OF THE INVENTION

It is therefore an object of the present invention to prepare an enantiomerically enriched β-amino acid derivative, in particular a β-amino ester, which will be useful for the synthesis of enantiomerically enriched sitagliptin free base (01) and its salts, by a simple, reliable, convenient and commercially acceptable process.

It is another object of the present invention to provide enantiomerically enriched β-amino acid derivatives, such as β-amino esters, and processes to prepare them, where said derivatives will be useful as intermediates for the synthesis of enantiomerically enriched sitagliptin free base (01) and its salts, by using a simple and reliable resolution technique, typically involving an inexpensive and readily available resolving agent.

It is yet another object of the present invention to provide pharmaceutical compositions and their use, wherein the compositions comprise sitagliptin free base (01) or its salts, such as the dihydrogen phosphate salt (02), obtained by the processes of the present invention.

DEFINITIONS

For the purposes of the present invention, a compound with one or more chiral centres is "enantiomerically enriched", if it comprises more than 75% of one stereoisomer, preferably more than 80%, preferably more than 85%, preferably more than 90%, preferably more than 95%. Accordingly, the term "enantiomerically enriched β-amino acid derivatives" encompasses, for example, "enantiomerically enriched (R)-sitagliptin (01) or its dihydrogen phosphate salt (02)" which comprises more than 75% of the (R)-stereoisomer and less than 25% of the (S)-stereoisomer. Similarly, the term "enantiomerically enriched β-amino acid derivative salt" encompasses, for example, "enantiomerically enriched (R)-β-amino acid derivative (R)-mandelate" which comprises more than 75% of the (R),(R)-stereoisomer and less than 25% of the (S),(R)-, (R),(S)- and (S),(S)-stereoisomers.

For the purposes of the present invention, a compound with one or more chiral centres is "racemic", if it comprises each stereoisomer relative to each other stereoisomer in a ratio of from 1:1.5 to 1.5:1. This means that a compound with one chiral centre is "racemic", if it comprises 40-60% of each of the two stereoisomers. A compound with two chiral centres is "racemic", if it comprises 20-30% of each of the four stereoisomers etc. Accordingly, the term "racemic β-amino acid derivative (03)" encompasses, for example, "racemic sitagliptin or its dihydrogen phosphate salt" which comprises (R)-sitagliptin or its dihydrogen phosphate salt and (S)-sitagliptin or its dihydrogen phosphate salt in a ratio of from 60:40 to 40:60.

For the purposes of the present invention, the term "an enantiomer" of an optically active acid such as tartaric acid, camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl)phthalamic acid, quinic acid, di-O-isopropylidene-2-oxo-L-gulonic acid, 2-hydroxy-4-isopropenyl-1-methyl-cyclohexane-1-sulphonic acid, mandelic acid, or a derivative thereof, or the term "an enantiomer" of a mandelic acid derivative, means that the acid or the derivative thereof comprises more than 95% of one stereoisomer, preferably more than 98%, preferably more than 99%, preferably more than 99.9%. Similarly, the term "(R)-(−)-mandelic acid" means that the mandelic acid comprises more than 95% of the (R)-stereoisomer, preferably more than 98%, preferably more than 99%, preferably more than 99.9%.

For the purposes of the present invention, a "chiral acid" or an "acid resolving agent" is any acid capable of forming a salt with the amino group of a β-amino acid derivative. Preferred acid resolving agents of the present invention are tartaric acid, camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl)phthalamic acid, quinic acid, di-O-isopropylidene-2-oxo-L-gulonic acid, 2-hydroxy-4-isopropenyl-1-methyl-cyclohexane-1-sulphonic acid, mandelic acid, and derivatives thereof, preferably (L)-tartaric acid, O,O'-di-p-toluoyl-(L)-tartaric acid, O,O'-dibenzoyl-(L)-tartaric acid, (R)-mandelic acid and its derivatives such as (R)-3-chloro-mandelic acid and (R)-3-bromo-mandelic acid, preferably (R)-mandelic acid.

For the purposes of the present invention, an "alkyl" group is defined as a monovalent saturated hydrocarbon, which may be straight-chained or branched, or be or include cyclic groups. An alkyl group may optionally be substituted, and may optionally include one or more heteroatoms N, O or S in its carbon skeleton. Preferably an alkyl group is straight-chained or branched. Preferably an alkyl group is not substituted. Preferably an alkyl group does not include any heteroatoms in its carbon skeleton. Examples of alkyl groups are methyl, ethyl, n-propyl, i-propyl, n-butyl, i-butyl, t-butyl, n-pentyl, cyclopentyl, cyclohexyl and cycloheptyl groups. Preferably an alkyl group is a $C_{1-12}$ alkyl group, preferably a $C_{1-6}$ alkyl group. Preferably a cyclic alkyl group is a $C_{3-12}$ cyclic alkyl group, preferably a $C_{5-7}$ cyclic alkyl group.

An "alkenyl" group is defined as a monovalent hydrocarbon, which comprises at least one carbon-carbon double bond, which may be straight-chained or branched, or be or include cyclic groups. An alkenyl group may optionally be substituted, and may optionally include one or more heteroatoms N, O or S in its carbon skeleton. Preferably an alkenyl group is straight-chained or branched. Preferably an alkenyl group is not substituted. Preferably an alkenyl group does not include any heteroatoms in its carbon skeleton. Examples of alkenyl groups are vinyl, allyl, but-1-enyl, but-2-enyl, cyclohexenyl and cycloheptenyl groups. Preferably an alkenyl group is a $C_{2-12}$ alkenyl group, preferably a $C_{2-6}$ alkenyl group. Preferably a cyclic alkenyl group is a $C_{3-12}$ cyclic alkenyl group, preferably a $C_{5-7}$ cyclic alkenyl group.

An "alkynyl" group is defined as a monovalent hydrocarbon, which comprises at least one carbon-carbon triple bond, which may be straight-chained or branched, or be or include cyclic groups. An alkynyl group may optionally be substituted, and may optionally include one or more heteroatoms N, O or S in its carbon skeleton. Preferably an alkynyl group is straight-chained or branched. Preferably an alkynyl group is not substituted. Preferably an alkynyl group does not include any heteroatoms in its carbon skeleton. Examples of alkynyl groups are ethynyl, propargyl, but-1-ynyl and but-2-ynyl groups. Preferably an alkynyl group is a $C_{2-12}$ alkynyl group, preferably a $C_{2-6}$ alkynyl group. Preferably a cyclic alkynyl group is a $C_{5-12}$ cyclic alkynyl group.

An "aryl" group is defined as a monovalent aromatic hydrocarbon. An aryl group may optionally be substituted, and may optionally include one or more heteroatoms N, O or S in its carbon skeleton.

For the purposes of the present invention, where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl.

The terms "sitagliptin" and "(R)-sitagliptin" are used interchangeably herein throughout the description and claims, and mean sitagliptin and/or any salt, hydrate or solvate thereof unless specified otherwise. Similarly, the term "(S)-sitagliptin", referring to the enantiomer of (R)-sitagliptin, means (S)-sitagliptin and/or any salt, hydrate or solvate thereof unless specified otherwise.

SUMMARY OF THE INVENTION

A first aspect of the present invention provides a process for the preparation of sitagliptin, or a pharmaceutically acceptable salt thereof, comprising resolution of a racemic β-amino acid, or a derivative thereof, with an acid resolving agent. Preferably, the β-amino acid derivative is a β-amino ester or a β-amino amide. More preferably, the β-amino acid derivative is a β-amino ester.

Preferably, the β-amino acid derivative is an alkyl, alkenyl, alkynyl, aryl or arylalkyl ester. More preferably, the β-amino acid derivative is a $C_1$ to $C_6$ alkyl ester or a benzyl ester or a substituted benzyl ester. More preferably, the β-amino acid derivative is a $C_1$ to $C_6$ alkyl ester, preferably a methyl or ethyl ester. Most preferably, the β-amino acid derivative is a methyl ester.

Preferably, the β-amino acid is 3-amino-4-(2,4,5-trifluorophenyl)butanoic acid or a derivative thereof. Preferably, the derivative is an ester and most preferably the derivative is methyl 3-amino-4-(2,4,5-trifluorophenyl)butanoate.

Preferably, the resolving agent used in the first aspect of the present invention is an enantiomer of mandelic acid, tartaric acid, camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl)phthalamic acid, quinic acid, di-O-isopropylidene-2-oxo-L-gulonic acid, 2-hydroxy-4-isopropenyl-1-methyl-cyclohexane-1-sulphonic acid, or a derivative thereof. Preferably, the resolving agent is an enantiomer of mandelic acid, such as (R)-(−)-mandelic acid or (S)-(+)-mandelic acid.

Preferably, the process according to the first aspect of the present invention comprises the steps of:
(a) treating a racemic β-amino acid, or a derivative thereof, with an acid resolving agent, preferably (R)-(−)-mandelic acid, or a derivative thereof, to obtain an enantiomerically enriched salt;
(b) optionally crystallising the enantiomerically enriched salt; and
(c) dissolving or suspending the enantiomerically enriched salt obtained in step (a) or (b) in an organic solvent or water or a mixture thereof, and adjusting the pH of the solution or suspension with a base to obtain an enantiomerically enriched β-amino acid or derivative thereof.

Preferably, the base used in step (c) is selected from an organic base, an inorganic base or a mixture thereof.

Preferably, the base used in step (c) is an organic base, such as an amine preferably selected from methylamine, dimethylamine, trimethylamine, ethylamine, diethylamine, triethylamine, N,N-diisopropylethylamine, cyclohexylamine, or a mixture thereof.

Preferably, the base used in step (c) is an inorganic base, such as ammonia, a metal hydroxide, a metal carbonate or a mixture thereof. Preferably, the metal hydroxide is sodium hydroxide, potassium hydroxide or lithium hydroxide, and/or the metal carbonate is sodium carbonate, lithium carbonate or calcium carbonate.

Preferably, step (a) is carried out in an organic solvent, optionally in the presence of water. The organic solvent is preferably selected from a protic or an aprotic solvent or a mixture thereof. More preferably, the organic solvent is an alcohol, a ketone, an ether, an alkane, a cycloalkane, a formamide, an acetate, a halogenated solvent or a mixture thereof. More preferably, the organic solvent is an alcohol preferably selected from methanol, ethanol, n-propanol, isopropanol, n-butanol, i-butanol, t-butanol, 2-pentanol, 3-pentanol, 4-penten-2-ol, 1,6-hexanediol, 1-hexanol, 5-hexen-1-ol, glycerol, 1-heptanol, 2-heptanol, 1-octanol, 2-octanol, 3-octanol or a mixture thereof. Most preferably, the alcohol is isopropanol.

If required, the solvent used in step (a) is a mixture comprising an alcohol and at least 0.1 to 20% water, preferably a mixture of an alcohol and 0.5 to 5% water.

Preferably, the process according to the first aspect of the present invention is a process for the preparation of sitagliptin (01) or sitagliptin dihydrogen phosphate salt (02), preferably sitagliptin dihydrogen phosphate salt (02).

A second aspect of the present invention provides an ester of (Z)-3-amino-4-(2,4,5-trifluorophenyl)but-2-enoic acid or a salt thereof. The ester is preferably an alkyl, alkenyl, alkynyl, aryl or arylalkyl ester and is most preferably methyl(Z)-3-amino-4-(2,4,5-trifluorophenyl)but-2-enoate or a salt thereof.

A third aspect of the present invention provides an ester of (3RS)-3-amino-4-(2,4,5-trifluorophenyl)butanoic acid or a salt thereof. The ester is preferably an alkyl, alkenyl, alkynyl, aryl or arylalkyl ester and is most preferably methyl(3RS)-3-amino-4-(2,4,5-trifluorophenyl)butanoate or a salt thereof.

A fourth aspect of the present invention provides an ester of (3R)-3-amino-4-(2,4,5-trifluorophenyl)butanoic acid or a salt thereof. The ester is preferably an alkyl, alkenyl, alkynyl, aryl or arylalkyl ester and is most preferably methyl(3R)-3-amino-4-(2,4,5-trifluorophenyl)butanoate or a salt thereof.

A fifth aspect of the present invention provides a process for the preparation of sitagliptin (01), or a pharmaceutically acceptable salt thereof, wherein the process involves a compound according to the second, third or fourth aspects of the present invention. Preferably, the sitagliptin (01) is in the form of its dihydrogen phosphate salt (02).

A sixth aspect of the present invention provides sitagliptin (01), or a pharmaceutically acceptable salt thereof (such as the dihydrogen phosphate salt (02)), as prepared by a process according to the first or fifth aspect of the present invention. Preferably the sitagliptin (01) or the pharmaceutically acceptable salt thereof has an enantiomeric purity of 99% or more, 99.5% or more, 99.9% or more, or 99.99% or more (as measured by chiral HPLC) and a chemical purity of 99% or more, 99.5% or more, 99.9% or more, or 99.99% or more (as measured by HPLC).

The sixth aspect of the present invention also provides sitagliptin (01), or a pharmaceutically acceptable salt thereof (such as the dihydrogen phosphate salt (02)), having an enantiomeric purity of 99% or more, 99.5% or more, 99.9% or more, or 99.99% or more (as measured by chiral HPLC).

The sixth aspect of the present invention also provides sitagliptin (01), or a pharmaceutically acceptable salt thereof (such as the dihydrogen phosphate salt (02)), having a chemical purity of 99% or more, 99.5% or more, 99.9% or more, or 99.99% or more (as measured by HPLC).

Preferably the sitagliptin (01) or the pharmaceutically acceptable salt thereof according to the sixth aspect of the present invention is suitable for use in medicine, preferably for treating or preventing a disease or condition for which an inhibitor of dipeptidyl peptidase-IV is effective, preferably for treating or preventing diabetes, hyperglycemia, insulin resistance, obesity, or high blood pressure, preferably for treating or preventing diabetes type-2.

A seventh aspect of the present invention provides a pharmaceutical composition comprising sitagliptin (01), or a pharmaceutically acceptable salt thereof, according to the sixth aspect of the present invention.

An eighth aspect of the present invention provides the use of sitagliptin (01) or a pharmaceutically acceptable salt thereof according to the sixth aspect of the present invention, or the use of the pharmaceutical composition according to the seventh aspect of the present invention, in the manufacture of a medicament for the treatment or prevention of a disease or condition for which an inhibitor of dipeptidyl peptidase-IV is effective. Preferably, the use according to the eighth aspect of the present invention is in the treatment or prevention of diabetes, hyperglycemia, insulin resistance, obesity, or high blood pressure, more preferably in the treatment or prevention of diabetes type-2.

A ninth aspect of the present invention provides a method of treating or preventing a disease or condition for which an inhibitor of dipeptidyl peptidase-IV is effective, the method comprising administering to a patient in need thereof a therapeutically or prophylactically effective amount of sitagliptin (01) or a pharmaceutically acceptable salt thereof according to the sixth aspect of the present invention, or a therapeutically or prophylactically effective amount of the pharmaceutical composition according to the seventh aspect of the present invention. Preferably, the method is for the treatment or prevention of diabetes, hyperglycemia, insulin resistance, obesity, or high blood pressure. More preferably, the method is for the treatment or prevention of diabetes type-2. Preferably the patient is a mammal, preferably a human.

If required, in the use according to the eighth aspect of the present invention or in the method according to the ninth aspect of the present invention, the sitagliptin (01), or a pharmaceutically acceptable salt thereof, is used in combination with one or more other active pharmaceutical ingredients. The other active ingredient(s) may be administered separately or in the same pharmaceutical composition. Preferably, the other active ingredient(s) is selected from insulin sensitizers such as glitazones (such as troglitazone, pioglitazone, englitazone and rosiglitazone); fenofibric acid derivatives (such as gemfibrozil, clofibrate, fenofibrate and bezafibrate); biguanides (such as metformin and phenformin); sulfonylureas (such as glipizide); or mixtures thereof.

BRIEF DESCRIPTION OF THE ACCOMPANYING FIGURES

FIGS. 1-4 outline prior art processes for the preparation of sitagliptin or a pharmaceutically acceptable salt thereof.

Figure 5:
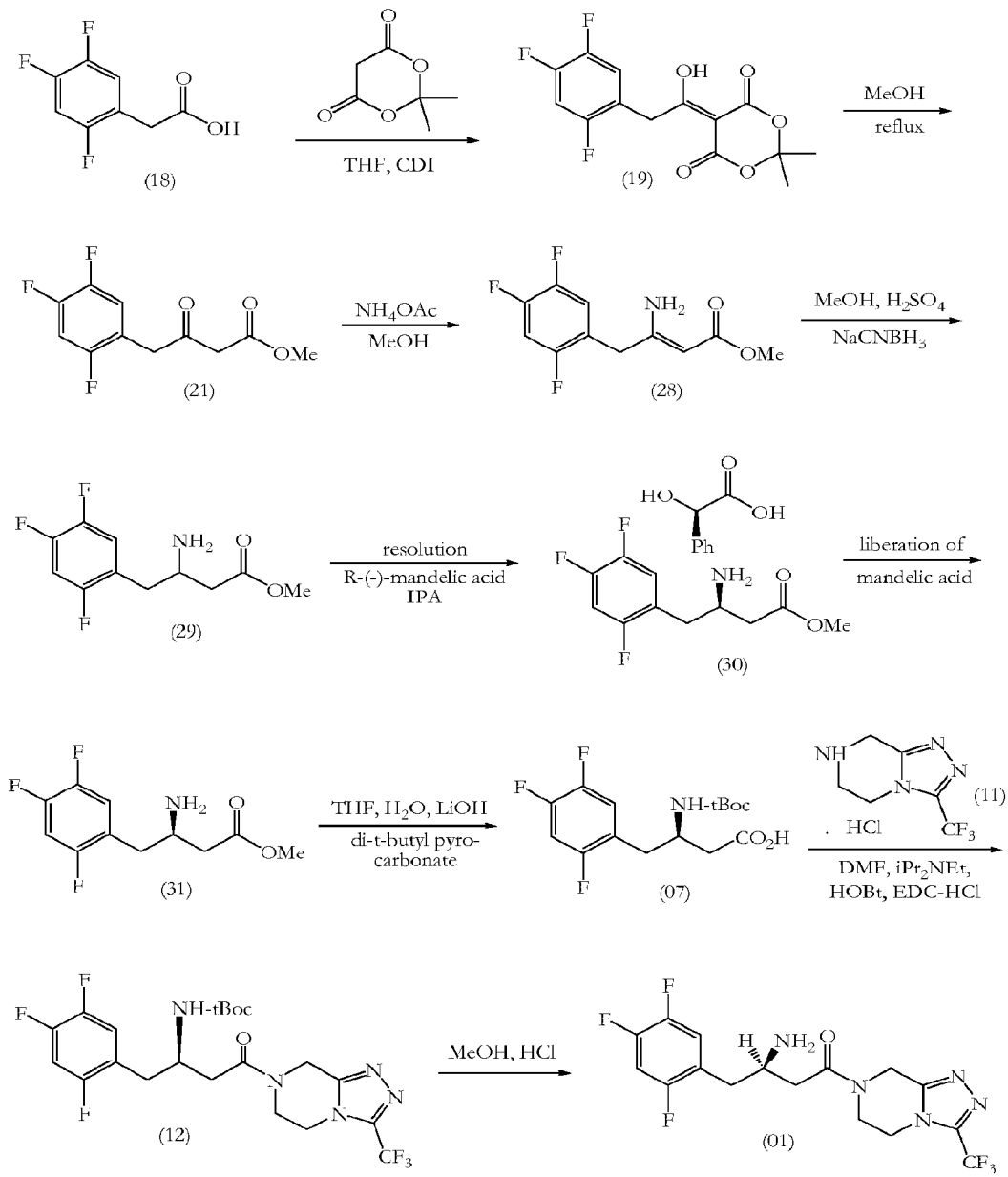

FIG. 5 outlines a particularly preferred embodiment of the process of the present invention for the preparation of sitagliptin or a pharmaceutically acceptable salt thereof.

DETAILED DESCRIPTION OF THE INVENTION

The present invention comprises a process for the preparation of sitagliptin free base (01) and its salts, by a simple, reliable, convenient and commercially acceptable process, which includes the following advantages:

The resolving agents used, preferably an enantiomer of mandelic acid or a derivative thereof, are inexpensive and easily available.

The process can be carried out under mild reaction conditions.

An excellent enantiomeric purity is achieved in the resolution step (98-99% or more, typically 99.25-99.75% or more).

The process is convenient and easy to carry out.

The isolation of the enantiomerically enriched β-amino ester is convenient.

The enantiomerically enriched β-amino ester obtained is of high enough quality to meet the requirements of the ICH guidelines when converted into sitagliptin (01) and/or a salt thereof, such as sitagliptin dihydrogen phosphate (02).

The process is particularly suitable for commercial scale manufacture.

The present invention provides a simple, convenient, and inexpensive process of preparing enantiomerically enriched sitagliptin free base (01) and sitagliptin dihydrogen phosphate (02), using an enantiomerically enriched β-amino acid derivative or β-amino ester.

A preferred embodiment of the present invention involves the process of resolving racemic β-amino ester (04) using an acid resolving agent, such as (R)-(−)-mandelic acid or a derivative thereof, to obtain enantiomerically enriched (R)-β-amino ester (4a), wherein R is an alkyl, alkenyl, alkynyl, aryl or arylalkyl group.

Other preferred acid resolving agents are enantiomers of tartaric acid, camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl) phthalamic acid, quinic acid, di-O-isopropylidene-2-oxo-L-gulonic acid, 2-hydroxy-4-isopropenyl-1-methyl-cyclohexane-1-sulphonic acid, or a derivative thereof, or an enantiomer of mandelic acid or a derivative thereof. Preferably the enantiomer of mandelic acid is (R)-(−)-mandelic acid.

Preferably the enantiomerically enriched β-amino acid derivative or β-amino ester obtained is converted into enantiomerically enriched sitagliptin base (01) or its dihydrogen phosphate salt (02).

In a preferred embodiment of the first aspect of the present invention, the process comprises the steps of:
(a) treating a racemic β-amino acid derivative (03) with an enantiomer of mandelic acid or a derivative thereof to obtain an enantiomerically enriched β-amino acid derivative salt;
(b) optionally crystallising the enantiomerically enriched β-amino acid derivative salt; and
(c) dissolving or suspending the enantiomerically enriched β-amino acid derivative salt obtained in step (a) or (b) in an organic solvent or water or a mixture thereof, and adjusting the pH of the solution or suspension with a base to obtain an enantiomerically enriched β-amino acid derivative.

In another preferred embodiment of the present invention, the process comprises the steps of:
(a) treating a racemic β-amino ester (04) with (R)-(−)-mandelic acid or a derivative thereof to obtain an enantiomerically enriched β-amino ester (4a) salt i.e. β-amino ester (4a) (R)-(−)-mandelate or a derivative thereof, wherein R is an alkyl, alkenyl, alkynyl, aryl or arylalkyl group;
(b) optionally crystallising the enantiomerically enriched β-amino ester (4a) (R)-(−)-mandelate or the derivative thereof; and
(c) dissolving or suspending the enantiomerically enriched β-amino ester (4a) (R)-(−)-mandelate or the derivative thereof obtained in step (a) or (b) in an organic solvent or water or a mixture thereof, and adjusting the pH of the solution or suspension with a base to obtain an enantiomerically enriched β-amino ester.

In a further preferred embodiment of the present invention, the process comprises the steps of:
(a) treating racemic methyl(3RS)-3-amino-4-(2,4,5-trifluorophenyl)butanoate (29) or a derivative thereof with (R)-(−)-mandelic acid or a derivative thereof to obtain enantiomerically enriched methyl(3R)-3-amino-4-(2,4,5-trifluorophenyl)butanoate (R)-(−)-mandelate (30) or a derivative thereof;
(b) optionally crystallising the enantiomerically enriched methyl(3R)-3-amino-4-(2,4,5-trifluorophenyl)butanoate (R)-(−)-mandelate (30) or the derivative thereof; and
(c) dissolving or suspending the enantiomerically enriched methyl(3R)-3-amino-4-(2,4,5-trifluorophenyl)butanoate (R)-(−)-mandelate (30) or the derivative thereof obtained in step (a) or (b) in an organic solvent or water or a mixture thereof, and adjusting the pH of the solution or suspension with a base to obtain enantiomerically enriched methyl (3R)-3-amino-4-(2,4,5-trifluorophenyl)butanoate (31).

Preferably the acid resolving agent, such as the enantiomer of mandelic acid or a derivative thereof, used in step (a) of these preferred embodiments, is used in an amount of 0.4 to 10 equivalents, preferably in an amount of 0.5 to 2.05 equivalents, relative to the racemic β-amino acid derivative (03) or relative to the racemic β-amino ester (04).

Preferably step (a) of these preferred embodiments is carried out in an organic solvent in the presence or absence of water. Preferably in step (b) of these preferred embodiments, the enantiomerically enriched β-amino acid derivative or β-amino ester salt is crystallised from an organic solvent in the presence or absence of water. The organic solvent may be a protic or aprotic solvent. Preferably the organic solvent is an alcohol, a ketone, an ether, an alkane, a cycloalkane, a formamide, an acetate, a halogenated solvent or a mixture thereof.

Step (b) of the preferred embodiments typically involves crystallisation from a solvent mixture comprising an alcohol and at least 0.10-15% water.

Step (c) of these preferred embodiments is typically carried out in an organic solvent or water or a mixture thereof.

Preferably, the enantiomerically enriched β-amino acid derivative or β-amino ester salt is a salt of tartaric acid, camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl)phthalamic acid, quinic acid, di-O-isopropylidene-2-oxo-L-gulonic acid, 2-hydroxy-4-isopropenyl-1-methyl-cyclohexane-1-sulphonic acid, O,O'-di-p-toluoyl-(L)-tartaric acid (including O,O'-di-p-toluoyl-(L)-tartaric acid monohydrate), O,O'-dibenzoyl-(L)-tartaric acid, mandelic acid, (R)-3-chloromandelic acid, or (R)-3-bromo-mandelic acid. More preferably, the enantiomerically enriched β-amino acid derivative or β-amino ester salt is a salt of (R)-(−)-mandelic acid or a derivative thereof.

Preferably, the base used in step (c) of these preferred embodiments is an organic or an inorganic base. Preferably, the organic base is an amine, preferably methylamine, dimethylamine, trimethylamine, ethylamine, diethylamine, diethylamine, N,N-diisopropylethylamine, cyclohexylamine, or a mixture thereof, preferably N,N-diisopropylethylamine. Preferably, the inorganic base is ammonia, a metal hydroxide (such as sodium hydroxide, potassium hydroxide or lithium hydroxide), a metal carbonate (such as sodium carbonate, lithium carbonate or calcium carbonate), or a mixture thereof. Preferably, the pH of the solution or suspension is adjusted to 4 to 9, preferably 8 to 9. Preferably, step (c) is carried out at a temperature of 0-30° C., preferably 20-30° C.

In all embodiments of the process of the present invention, preferably the enantiomerically enriched β-amino acid derivative, β-amino ester, sitagliptin and its salts are prepared on an industrial scale, preferably in batches of 0.5 kg or more, 1 kg or more, 10 kg or more, or 50 kg or more.

In all embodiments of the process of the present invention, preferably the temperature throughout the reaction is less than 100° C., preferably less than 90° C.

In all embodiments of the process of the present invention, preferably the enantiomerically enriched β-amino acid derivative and β-amino ester is obtained in a molar yield of at least 60% to 65%.

Preferably, the enantiomerically enriched β-amino acid derivative salt and β-amino ester salt obtained has an enantiomeric purity of 93% or more, 95% or more, 97% or more, 98.5% or more, or 99.9% or more (as measured by chiral HPLC). Preferably, the enantiomerically enriched β-amino acid derivative salt and β-amino ester salt obtained has a chemical purity of 95% or more, 98% or more, 99% or more, 99.5% or more, or 99.9% or more (as measured by HPLC).

Preferably, the enantiomerically enriched β-amino acid derivative and β-amino ester obtained has an enantiomeric purity of 93% or more, 95% or more, 97% or more, 98.5% or more, or 99.9% or more (as measured by chiral HPLC). Preferably, the enantiomerically enriched β-amino acid derivative and β-amino ester obtained has a chemical purity of 95% or more, 98% or more, 99% or more, 99.5% or more, or 99.9% or more (as measured by HPLC).

Preferably, the sitagliptin free base (01) and its salts, such as the dihydrogen phosphate salt (02), are prepared with an enantiomeric purity of 99% or more, 99.5% or more, 99.9% or more, or 99.99% or more (as measured by chiral HPLC) and a chemical purity of 99% or more, 99.5% or more, 99.9% or more, or 99.99% or more (as measured by HPLC).

A particularly preferred embodiment of the process of the present invention for the preparation of sitagliptin is outlined in Scheme 5.

Preferred embodiments of the present invention comprise the following steps:
(1) Preparation of Meldrum's adduct (19).
(2) Preparation of methyl 4-(2,4,5-trifluorophenyl)acetoacetate (21).
(3) Preparation of methyl(Z)-3-amino-4-(2,4,5-trifluorophenyl)but-2-enoate (28).
(4) Preparation of racemic methyl(3RS)-3-amino-4-(2,4,5-trifluorophenyl)butanoate (29).
(5) Resolution of racemic methyl(3RS)-3-amino-4-(2,4,5-trifluorophenyl)butanoate (29).
(6) Preparation of (3R)-3-[N-(tert-butoxycarbonyl)amino]-4-(2,4,5-trifluorophenyl)butanoic acid (07).
(7) Preparation of 7-[(3R)-3-[N-(tert-butoxycarbonyl)amino]-4-(2,4,5-trifluorophenyl)-butanoyl]-3-(trifluoromethyl)-5,6,7,8-tetrahydro-1,2,4-triazolo[4,3-a]pyrazine (12).
(8) Preparation of enantiomerically enriched sitagliptin free base (01).

(1) Preparation of Meldrum's Adduct (19)

Meldrum's adduct formation was carried out by using a process reported in the literature. 2,4,5-Trifluorophenylacetic acid (18) was treated with an acid activating group, preferably N,N'-carbonyldiimidazole (CDI), preferably in ethereal solvents, to form a complex. The complex was further treated with Meldrum's acid and the entire reaction sequence was carried out in a temperature range of 25-55° C. The Meldrum's adduct was further isolated by aqueous work up procedures, which preferably involved complete removal of the solvent, acidification of the reaction mixture, extraction using halogenated solvent, washing of the organic layer with water and distillation of the solvent to afford the product.

(2) Preparation of methyl 4-(2,4,5-trifluorophenyl)acetoacetate (21)

The Meldrum's adduct (19) was treated with alcoholic solvents, preferably with methanol, at higher temperature, preferably at 60-65° C. The ester formed was preferably isolated by an aqueous extractive work up procedure, which preferably involved complete removal of the solvent, basification of the reaction mixture, extraction using halogenated solvent, washing of the organic layer with water and distillation of the solvent to afford the product.

(3) Preparation of methyl(Z)-3-amino-4-(2,4,5-trifluorophenyl)but-2-enoate (28)

Methyl 4-(2,4,5-trifluorophenyl)acetoacetate (21) was treated with anhydrous ammonium acetate in an alcoholic solvent, preferably methanol, and preferably at higher temperature, preferably at 60-65° C. The methyl(Z)-3-amino-4-(2,4,5-trifluorophenyl)but-2-enoate (28) formed was preferably isolated by complete removal of the solvent under reduced pressure, separation of excess of ammonium acetate by using a polar organic solvent such as ethyl acetate, distillation of the polar organic solvent and triturating the product with non-polar solvents like hexane.

(4) Preparation of racemic methyl(3RS)-3-amino-4-(2,4,5-trifluorophenyl)butanoate (29)

Racemic methyl(3RS)-3-amino-4-(2,4,5-trifluorophenyl)butanoate (29) was prepared by reducing the methyl(Z)-3-amino-4-(2,4,5-trifluorophenyl)but-2-enoate (28) with a reducing agent such as an alkali metal borohydride. The reducing agent is preferably sodium cyanoborohydride. The reduction is preferably performed in the presence of an organic protic solvent or ethereal solvent. The temperature of this reaction should preferably be less than 0 to −5° C. during the addition of the sodium cyanoborohydride. In addition, there should be strict control on the amount of water present during the reaction by using water-scavenging agents. The amount of sodium cyanoborohydride used for this reduction is preferably 0.5 to 10 equivalents.

(5) Preparation of methyl(3R)-3-amino-4-(2,4,5-trifluorophenyl)butanoate (31)

The resolution of racemic amine (29) involves two or three stages:
(a) treating methyl(3RS)-3-amino-4-(2,4,5-trifluorophenyl)butanoate (29) with an acid resolving agent, such as (R)-(−)-mandelic acid or a derivative thereof, to obtain an enantiomerically enriched crude methyl(3R)-3-amino-4-(2,4,5-trifluorophenyl)butanoate salt such as the (R)-(−)-mandelate salt;
(b) optionally crystallising the enantiomerically enriched crude methyl(3R)-3-amino-4-(2,4,5-trifluorophenyl)butanoate salt to obtain an enantiomerically enriched pure methyl(3R)-3-amino-4-(2,4,5-trifluorophenyl)butanoate salt, such as the (R)-(−)-mandelate salt (30); and
(c) dissolving or suspending the enantiomerically enriched salt, such as methyl(3R)-3-amino-4-(2,4,5-trifluorophenyl)butanoate (R)-(−)-mandelate (30) or a derivative thereof, obtained from step (a) or (b) in an organic solvent or water or a mixture thereof, and adjusting the pH of the solution or suspension with a base to obtain enantiomerically enriched methyl(3R)-3-amino-4-(2,4,5-trifluorophenyl)butanoate (31).

Preferably the acid resolving agent, for example (R)-(−)-mandelic acid or a derivative thereof, used in step (a) of these preferred embodiments is used in an amount of 0.4 to 10 equivalents, preferably in an amount of 0.5 to 2.05 equivalents, relative to the racemic methyl(3RS)-3-amino-4-(2,4,5-trifluorophenyl)butanoate (29).

In step (a) the acid resolving agent may be added to a solution or suspension of methyl(3RS)-3-amino-4-(2,4,5-trifluorophenyl)butanoate (29) either as a solid or in solution. A preferred solution is prepared in an organic protic or aprotic solvent, in a mixture of organic protic or aprotic solvents, in water, or in a mixture of one or more organic protic or aprotic solvents and water. Preferably the organic protic or aprotic solvent is an alcohol, a ketone, an ether, an alkane, a cycloalkane, a formamide, an acetate, a halogenated solvent or a mixture thereof. Preferably, (R)-(−)-mandelic acid solution is prepared in isopropanol.

The preferred temperature for the addition of the acid resolving agent, such as (R)-(−)-mandelic acid, is −10 to 90° C., preferably 25-30° C.

After the addition of the acid resolving agent, such as (R)-(−)-mandelic acid, the reaction mixture is preferably stirred at a temperature of −10 to 90° C., preferably −10 to 30° C., and more preferably at 25-30° C., to obtain a clear solution. The clear solution is preferably stirred for a period of 5 minutes to 10 hours, preferably stirred at a temperature of −10 to 30° C. for 5 minutes to 10 hours, preferably at 25-30° C. for about 3-4 hours, to precipitate the enantiomerically enriched salt, such as methyl(3R)-3-amino-4-(2,4,5-trifluorophenyl) butanoate (R)-(−)-mandelate. The enantiomerically enriched salt is isolated preferably by filtration, preferably washed with isopropanol and preferably dried in a vacuum oven at a temperature of 40-60° C., more preferably at 40-45° C., for about 4-5 hours.

In a preferred resolution procedure, in step (a), racemic methyl(3RS)-3-amino-4-(2,4,5-trifluorophenyl)butanoate (29) is treated with (R)-(−)-mandelic acid to obtain enantiomerically enriched crude methyl(3R)-3-amino-4-(2,4,5-trifluorophenyl)butanoate (R)-(−)-mandelate (30) with 93-99% enantiomeric purity (R-isomer as measured by chiral HPLC). The molar yield of the enantiomerically enriched crude methyl(3R)-3-amino-4-(2,4,5-trifluorophenyl)butanoate (R)-(−)-mandelate (30) is preferably at least 60-65%. During step (b), the enantiomeric purity of the enantiomerically enriched crude methyl(3R)-3-amino-4-(2,4,5-trifluorophenyl)butanoate (R)-(−)-mandelate salt (30) is increased up to 99.75-100% (R-isomer as measured by chiral HPLC) to obtain enantiomerically enriched pure methyl(3R)-3-amino-4-(2,4,5-trifluorophenyl)butanoate (R)-(−)-mandelate (30).

Preferably step (a) and step (b) of these preferred embodiments are carried out in an organic solvent optionally in the presence of water. The organic solvent may be a protic or aprotic solvent. Preferably the organic solvent is an alcohol, a ketone, an ether, an alkane, a cycloalkane, a formamide, an acetate, a halogenated solvent or a mixture thereof. The solvent is preferably an alcohol, preferably selected from methanol, ethanol, n-propanol, isopropanol, n-butanol, i-butanol, t-butanol, 2-pentanol, 3-pentanol, 4-penten-2-ol, 1,6-hexanediol, 1-hexanol, 5-hexen-1-ol, glycerol, 1-heptanol, 2-heptanol, 1-octanol, 2-octanol, or 3-octanol or a mixture thereof. The solvent is most preferably isopropanol.

Preferably in step (a) and step (b) of these preferred embodiments, the solvent mixture comprises alcohol:water in a ratio of 50:50 to 99.9:0.1, preferably in a ratio of 80:20 to 99.9:0.1. A preferred solvent mixture is isopropanol:water in a ratio of 80:20 to 99.9:0.1.

Step (c) of these preferred embodiments is carried out in an organic solvent or water or a mixture thereof, preferably in water as solvent.

The enantiomerically enriched β-amino ester, such as methyl(3R)-3-amino-4-(2,4,5-trifluorophenyl)butanoate (31), is preferably isolated by basification and extraction in organic solvent and distillation of the organic solvent at 40-60° C., preferably at 40-45° C. The enantiomeric purity of the enantiomerically enriched β-amino ester obtained, such as methyl(3R)-3-amino-4-(2,4,5-trifluorophenyl)butanoate (31), is preferably 99.5% or more, 99.8% or more, 99.9% or more, or 99.99% or more (as measured by chiral HPLC). The molar yield of the enantiomerically enriched β-amino ester obtained is preferably 90% or more.

In order to basify the solution or suspension of enantiomerically enriched β-amino ester salt, the pH is adjusted to 4 to 9, preferably 8 to 9. The pH is preferably adjusted by using an organic or inorganic base. Preferred organic bases are methylamine, dimethylamine, trimethylamine, ethylamine, diethylamine, triethylamine, N,N-diisopropylethylamine, or cyclohexylamine, preferably N,N-diisopropylethylamine. Preferred inorganic bases are ammonia; a metal hydroxide such as sodium hydroxide, potassium hydroxide, lithium hydroxide; a metal carbonate such as sodium carbonate, lithium carbonate, calcium carbonate; and a mixture thereof. The most preferred base is sodium carbonate.

The pH is preferably adjusted at a temperature of −10 to 30° C., preferably 20-25° C.

By following reaction conditions similar to those mentioned above using (R)-(−)-mandelic acid as resolving agent, resolution can also be achieved using an enantiomer of tartaric acid or a derivative thereof (such as O,O'-di-p-toluoyl-(L)-tartaric acid (including O,O'-di-p-toluoyl-(L)-tartaric acid monohydrate) or O,O'-dibenzoyl-(L)-tartaric acid), or an enantiomer of a derivative of mandelic acid (such as (R)-3-chloro-mandelic acid or (R)-3-bromo-mandelic acid), or an enantiomer of camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl) phthalamic acid, quinic acid, di-O-isopropylidene-2-oxo-L-gulonic acid, 2-hydroxy-4-isopropenyl-1-methyl-cyclohexane-1-sulphonic acid, or a derivative thereof.

By following reaction conditions similar to those mentioned above using (R)-(−)-mandelic acid as resolving agent, (S)-(+)-mandelic acid can be used for the resolution of racemic β-amino acid derivatives, racemic β-amino esters and racemic methyl(3RS)-3-amino-4-(2,4,5-trifluorophenyl)butanoate to obtain (S)-β-amino acid derivatives, (S)-β-amino esters and methyl(3S)-3-amino-4-(2,4,5-trifluorophenyl)butanoate. The methyl(3S)-3-amino-4-(2,4,5-trifluorophenyl) butanoate can be converted into (S)-sitagliptin and its dihydrogen phosphate salt.

By following reaction conditions similar to those mentioned above, resolution of racemic β-amino acid derivatives (03) can also be achieved.

(6) Preparation of (3R)-3-[N-(tert-butoxycarbonyl)amino]-4-(2,4,5-trifluorophenyl)butanoic acid (07)

The enantiomerically enriched methyl(3R)-3-amino-4-(2, 4,5-trifluorophenyl)butanoate (31) was converted into (3R)-3-[N-(tert-butoxycarbonyl)amino]-4-(2,4,5-trifluorophenyl)-butanoic acid (07) by hydrolysis and protection. Preferably the hydrolysis and protection are carried out in that order, preferably as a one-pot reaction. The methyl(3R)-3-amino-4-(2,4,5-trifluorophenyl)butanoate (31) was preferably hydrolysed using a metal hydroxide, preferably lithium hydroxide in ethereal solvents, more preferably tetrahydrofuran, in the presence or absence of water. The preferred time and temperature for this reaction is 5 minutes to 15 hours at 0-65° C., more preferably 8-10 hours at 25-30° C. After completion of the hydrolysis, the amino group was protected, preferably by using di-tert-butyl pyrocarbonate. The amino protection was carried out at 0-45° C. for 15 minutes to 10 hours, more preferably at 25-30° C. for 5-6 hours. The product was preferably isolated by aqueous and extractive work up procedures such as removal of the solvent, adjusting the pH to about 2 using a base such as $NaHSO_4$, extraction in an organic solvent such as ethyl acetate, washing of the organic layer, and distillation of the solvent to obtain the product.

(7) Preparation of 7-[(3R)-3-[N-(tert-butoxycarbonyl) amino]-4-(2,4,5-trifluorophenyl)-butanoyl]-3-(trifluoromethyl)-5,6,7,8-tetrahydro-1,2,4-triazolo[4,3-a]pyrazine (12)

(3R)-3-[N-(tert-Butoxycarbonyl)amino]-4-(2,4,5-trifluorophenyl)butanoic acid (07) was coupled with 3-trifluoromethyl-5,6,7,8-tetrahydro[1,2,4]triazolo[4,3-a]pyrazine hydrochloride (11) to obtain Boc-protected sitagliptin free base, 7-[(3R)-3-[N-(tert-butoxycarbonyl)amino]-4-(2,4,5-trifluorophenyl)butanoyl]-3-(trifluoromethyl)-5,6,7,8-tetrahydro-1,2,4-triazolo[4,3-a]pyrazine (12). The coupling was preferably carried out by using coupling agents such as EDC-HCl, 1-hydroxybenzotriazole and a suitable base such as N,N-diisopropylethylamine. The coupling was preferably carried out in an aprotic solvent such as N,N-dimethylformamide or N,N-dimethylacetamide at 0-30° C. for 1-12 hours, preferably at 25-30° C. for 8-10 hours. The Boc-protected sitagliptin free base (12) was preferably isolated by an aqueous work up procedure, preferably involving removal of N,N-dimethylformamide at 50-55° C. under reduced pressure followed by basification preferably using sodium carbonate, and extraction of the product into an organic solvent such as ethyl acetate. The Boc-protected sitagliptin free base (12) was preferably isolated by removal of the organic solvent under reduced pressure to obtain a white solid, which was preferably triturated with a non-polar solvent such as hexane.

(8) Preparation of Enantiomerically Enriched Sitagliptin Free Base (01)

Boc-protected sitagliptin free base (12) was preferably deprotected using acidic agents such as hydrochloric acid or trifluoroacetic acid. The deprotection was preferably carried out at 0-65° C., more preferably at 25-45° C., preferably in an alcoholic reaction solvent, preferably methanol, in the presence of hydrochloric acid. Sitagliptin free base (01) was preferably isolated by an aqueous work up procedure, which typically involved distillation of the reaction solvent under reduced pressure followed by basification using a base such as sodium carbonate, extraction in an organic solvent such as ethyl acetate, washing and removal of the organic layer. The crude product obtained may be further purified by acid base treatment by using orthophosphoric acid to obtain sitagliptin free base as an off-white solid, which can be converted into a crystalline solid by treatment with a solvent such as toluene.

The enantiomerically enriched sitagliptin free base (01) can be converted into any salt, such as sitagliptin dihydrogen phosphate (02), by conventional methods known to the skilled person.

In an analogous manner, the enantiomer of sitagliptin, herein called (S)-sitagliptin, can be prepared using (S)-(+)-mandelic acid as the acid resolving agent. A preferred method of preparing (S)-sitagliptin base and (S)-sitagliptin dihydrogen phosphate is using an analogous method as described herein starting from methyl(3S)-3-amino-4-(2,4,5-trifluorophenyl)butanoate, obtained by using (S)-(+)-mandelic acid.

The pharmaceutical composition according to the seventh aspect of the present invention can be a solution or a suspension, but is preferably a solid oral dosage form. Preferred oral dosage forms in accordance with the invention include tablets, capsules and the like which, optionally, may be coated if desired. Tablets can be prepared by conventional techniques, including direct compression, wet granulation and dry granulation. Capsules are generally formed from a gelatine material and can include a conventionally prepared granulate of excipients in accordance with the invention.

The pharmaceutical composition according to the present invention typically comprises one or more conventional pharmaceutically acceptable excipient(s) selected from the group comprising a filler, a binder, a disintegrant, a lubricant, and optionally further comprises at least one excipient selected from colouring agents, adsorbents, surfactants, film formers and plasticizers.

If the solid pharmaceutical formulation is in the form of coated tablets, the coating may be prepared from at least one film-former such as hydroxypropyl methyl cellulose, hydroxypropyl cellulose or methacrylate polymers which optionally may contain at least one plasticizer such as polyethylene glycols, dibutyl sebacate, triethyl citrate, and other pharmaceutical auxiliary substances conventional for film coatings, such as pigments and fillers.

Preferably the pharmaceutical compositions according to the present invention are in unit dosage form comprising sitagliptin in an amount of from 1 mg to 500 mg, such that the amount of sitagliptin administered is from 0.1 mg to 100 mg per kg per day.

The pharmaceutical compositions according to the seventh aspect of the present invention are for use in the treatment and prevention of diseases and conditions for which an inhibitor of dipeptidyl peptidase-IV is effective. Preferably, the use is in the treatment of diabetes, hyperglycemia, insulin resistance, obesity, and high blood pressure. More preferably, the use is in the treatment of diabetes type-2.

The sitagliptin or its salt can be used in combination with other active ingredients. Examples of other active ingredients that may be administered in combination with the compound of the present invention and either administered separately or in the same pharmaceutical composition, include but are not limited to other dipeptidyl peptidase IV (DP-IV) inhibitors; insulin sensitizers such as glitazones (such as troglitazone, pioglitazone, englitazone and rosiglitazone); fenofibric acid derivatives (such as gemfibrozil, clofibrate, fenofibrate and bezafibrate); biguanides (such as metformin and phenformin); sulfonylureas (such as glipizide); or mixtures thereof.

The details of the invention, its objects and advantages are illustrated below in greater detail by non-limiting examples.

EXAMPLES

Meldrum's Adduct (19)

2,4,5-Trifluorophenylacetic acid (500.0 gm, 2.63 mol) (18) was suspended in tetrahydrofuran (5.26 vol, 2.63 Ltr) at 25-30° C. and the reaction mixture was stirred for 10-15 minutes. To this clear solution, 1,1'-carbonyldiimidazole (1.5 eq, 639.68 gm) was charged in four lots and the reaction mixture was stirred for 2-3 hours at 25-30° C. After 2-3 hours stirring, Meldrum's acid (1.2 eq, 454.87 gm) was charged and the reaction mixture was heated for 6 hours at 50-55° C. After 6 hours heating at 50-55° C., the tetrahydrofuran was distilled out completely at 50-55° C. under reduced pressure to give a dark yellow coloured residue. The dark yellow residue was acidified by using a 1:1 mixture of 35% hydrochloric acid:water (0.5 vol, 250.0 ml) at 0-5° C. The product was extracted from the aqueous solution by using dichloromethane (3×5.0 vol, 3×2.5 Ltr). The combined dichloromethane layers were further washed with water (3×10.0 vol, 3×5.0 Ltr). After water washing, the dichloromethane was completely distilled under reduced pressure to give a dark yellow fluffy solid. The product was further washed with methanol (2.0 vol, 1.0 Ltr) at 0-5° C.

Molar Yield: 60-65% (505.0 gm)
Chemical Purity: 98-99.5% (as measured by HPLC)

Methyl 4-(2,4,5-trifluorophenyl)acetoacetate (21)

Meldrum's adduct (500.0 gm, 1.58 mol) (19) was charged in methanol (10.0 vol, 5.0 Ltr) at 25-30° C. and the partially clear solution was refluxed at 60-63° C. for 3-4 hours. After 3-4 hours refluxing, the methanol was completely distilled under reduced pressure at 45-50° C. to give a pale yellow coloured residue. The pale yellow coloured residue was further treated with 5% sodium carbonate solution (10.0 vol, 5.0 Ltr) to adjust the pH to 7-8. After pH adjustment, the product was extracted in dichloromethane (2×10.0 vol, 2×5.0 Ltr). The combined dichloromethane layers were further washed with water (3×2.5 vol, 3×1.25 Ltr). The dichloromethane was distilled under reduced pressure to give a pale yellow coloured oily product.

Molar Yield: 85-90% (350.0 gm)
Chemical Purity: 93-95% (as measured by HPLC)

Methyl(Z)-3-amino-4-(2,4,5-trifluorophenyl)but-2-enoate (28)

The methyl 4-(2,4,5-trifluorophenyl)acetoacetate (350.0 gm, 1.42 mol) (21) and ammonium acetate (6.0 eq, 657.0 gm) were charged in methanol (5.0 vol, 1.75 Ltr) and the solution was refluxed for 5-6 hours at 60-63° C. After 5-6 hours refluxing, the methanol was distilled out completely to give a pale yellow coloured residue. The pale yellow coloured residue was further stirred with ethyl acetate (20.0 vol, 7.0 Ltr) at 25-30° C. The precipitated ammonium acetate was filtered and the ethyl acetate was distilled out completely to give a pale yellow product. The product was further stirred with hexane (10.0 vol, 3.5 Ltr) at 25-30° C. for 1 hour, filtered and dried under reduced pressure at 45-50° C. for 4-5 hours.

Molar Yield: 85-90% (325.0 gm)
Chemical Purity: 96-97% (as measured by HPLC)

Methyl(3RS)-3-amino-4-(2,4,5-trifluorophenyl)butanoate (29)

The methyl(Z)-3-amino-4-(2,4,5-trifluorophenyl)but-2-enoate (350.0 gm, 1.42 mol) (28) was charged in methanol (10.0 vol, 3.5 Ltr) at 25-30° C. and the reaction was stirred for 10-15 minutes to give a clear solution. To the clear pale yellow solution, controlled addition of sulphuric acid (70.0 ml, 0.2 vol) was done at 0 to −10° C. and the clear solution was stirred for 10-15 minutes at 0 to −10° C. After 10-15 minutes stirring at 0 to −10° C., sodium cyanoborohydride (2.0 eq, 170.0 gm) was charged in 10 lots. The clear white suspension was stirred at 0 to −10° C. for 2 hours. The methanol was distilled completely at 45-50° C. under reduced pressure to give a pale yellow residue. The pale yellow residue was further treated with a 1:1 mixture of 35% hydrochloric acid: water at 0-5° C. to give pH 2. The suspension was stirred at 0-5° C. for 10-15 minutes and the suspension was further basified by using 20% sodium carbonate to give pH 8-9. The product was extracted in ethyl acetate (2×10.0 vol, 2×3.5 Ltr).

The combined ethyl acetate layers were washed with water (3×10.0 vol, 3×3.5 Ltr). The product was isolated by distillation of the ethyl acetate to give a pale yellow coloured oil.

Molar Yield: 75-80% (268 gm)
Chemical Purity: 78-85% (as measured by HPLC)

Methyl(3R)-3-amino-4-(2,4,5-trifluorophenyl)butanoate (R)-(−)-mandelate (30)

The methyl(3RS)-3-amino-4-(2,4,5-trifluorophenyl)butanoate (260 gm, 1.05 mol) (29) was charged in isopropanol (6.0 vol, 1.56 Ltr) at 25-30° C. and the reaction mixture was stirred for 15 minutes to give a clear solution. After 15 minutes stirring, controlled addition of a solution of (R)-(−)-mandelic acid [2.0 eq, 320 gm in 6.0 vol, 1.56 Ltr of isopropanol] was carried out. After completion of the addition, the reaction mixture was stirred at 25-30° C. for 3 hours to give enantiomerically enriched crude methyl(3R)-3-amino-4-(2,4,5-trifluorophenyl)butanoate (R)-(−)-mandelate as a white coloured product. The product was filtered, washed with isopropanol (1.0 vol, 260 ml), and dried in a vacuum oven at 40-45° C. for 4-5 hours to give enantiomerically enriched crude methyl(3R)-3-amino-4-(2,4,5-trifluorophenyl)butanoate (R)-(−)-mandelate (135 gm, molar yield: 64%). The dried enantiomerically enriched crude methyl(3R)-3-amino-4-(2,4,5-trifluorophenyl)butanoate (R)-(−)-mandelate product (135 gm) was charged in isopropanol (20.0 vol, 2.7 Ltr) at 25-30° C. and the white suspension was further heated at 75-80° C. for 0.5 hour to give a partially clear solution. The partially clear solution was made clear by the addition of water (2.0 vol, 270.0 ml) at 75-80° C. The clear solution was further stirred for 0.5 hour. After stirring for 0.5 hour, the clear solution was gradually cooled to 0-5° C. within 3 hours to give enantiomerically enriched pure methyl(3R)-3-amino-4-(2,4,5-trifluorophenyl)butanoate (R)-(−)-mandelate (30) as white coloured product. The product was filtered, washed with isopropanol (1.0 vol, 135.0 ml), and dried in a vacuum oven at 40-45° C. for 4-5 hours.

Molar Yield: 80-85% (113 gm)
Chemical Purity: 98-99.5% (as measured by HPLC)
Enantiomeric Purity: 99.25-99.75% (as measured by chiral HPLC)

Methyl(3R)-3-amino-4-(2,4,5-trifluorophenyl)butanoate (31)

The methyl(3R)-3-amino-4-(2,4,5-trifluorophenyl)butanoate (R)-(−)-mandelate (30) (113.0 gm) was taken in water (10.0 vol, 1.13 Ltr) and the suspension was stirred for 10-15 minutes. The suspension was further basified by using a 10% $Na_2CO_3$ solution (1.0 vol, 113.0 ml) until the pH of the reaction mixture reached 8-9. The product was extracted in ethyl acetate (2×10.0 vol, 2×1.13 Ltr). The combined ethyl acetate layers were further washed with water (2×10.0 vol, 2×1.13 Ltr). The product was isolated as a pale yellow oil by complete distillation of the ethyl acetate under reduced pressure at 45-50° C.

Molar Yield: 90-95% (65.0 gm)
Chemical Purity: 99-99.5% (as measured by HPLC)
Enantiomeric Purity: 99.25-99.75% (as measured by chiral HPLC)

(3R)-3-[N-(tert-butoxycarbonyl)amino]-4-(2,4,5-trifluorophenyl)butanoic acid (07)

The methyl(3R)-3-amino-4-(2,4,5-trifluorophenyl)butanoate (76.0 gm) (31) was charged in tetrahydrofuran (5.0 vol, 380.0 ml) and water (5.0 vol, 380.0 ml) at 25-30° C. The clear pale yellow solution was further chilled at 0-5° C. To the clear pale yellow solution, lithium hydroxide (3.0 eq, 38.73 gm) was charged at 0-5° C. and the reaction mixture was stirred at 25-30° C. for 9-10 hours. After stirring for 9-10 hours, di-tert-butyl pyrocarbonate (3.0 eq, 202.0 gm) was charged to the reaction mixture at 25-30° C. The white suspension was stirred for 6 hours before the tetrahydrofuran was distilled out completely to give an off-white residue. The residue was further treated 10% NaHSO$_4$ solution (5.0 vol, 380 ml) to give pH 2. The product was extracted in ethyl acetate (2×10.0 vol, 2×760 ml). The combined ethyl acetate layers were washed with water (2×10.0 vol, 2×760 ml). The white coloured product was isolated by complete distillation of the ethyl acetate under reduced pressure at 40-45° C. The white coloured product was further triturated with hexane (10.0 vol, 760.0 ml), filtered and dried in a vacuum oven at 45-50° C. for 4-5 hours.

Molar Yield: 80-85% (100.0 gm)
Chemical Purity: 96-98% (as measured by HPLC)

7-[(3R)-3-[N-(tert-butoxycarbonyl)amino]-4-(2,4,5-trifluorophenyl)butanoyl]-3-(trifluoro-methyl)-5,6,7,8-tetrahydro-1,2,4-triazolo[4,3-a]pyrazine (12)

To a solution of 3-trifluoromethyl-5,6,7,8-tetrahydro[1,2,4]triazolo[4,3-a]pyrazine hydrochloride (11) (1.0 eq, 28.0 gm), diisopropylethylamine (2.0 eq, 31.0 gm), 1-hydroxy-benzotriazole (1.2 eq, 22.0 gm), and EDC-HCl (1.2 eq, 28.0 gm) in N,N-dimethylformamide (4.0 vol, 160.0 ml), a solution of (3R)-3-[N-(tert-butoxycarbonyl)amino]-4-(2,4,5-trifluorophenyl)butanoic acid (07) (40.0 gm, 0.12 mol) in N,N-dimethylformamide (4.0 vol, 160.0 ml) was charged at 0-5° C. within 1 hour. The clear pale yellow solution was further stirred for 12 hours at 25-30° C. After stirring for 12 hours, the N,N-dimethylformamide was distilled out completely at 55-65° C. under reduced pressure to give a brown coloured residue. The brown coloured residue was further basified with 10% Na$_2$CO$_3$ solution (1.0 vol, 40.0 ml) and the product was extracted in ethyl acetate (3×10.0 vol, 3×400.0 ml). The combined ethyl acetate layers were washed with water, charcoalized and filtered, and the ethyl acetate was distilled out completely to give a white coloured product. The product was triturated with hexane (10.0 vol, 400.0 ml) and filtered at 25-30° C. The crude Boc-protected sitagliptin free base (12) was further purified by crystallising it from a mixture of isopropanol (20.0 vol) and water (2.0 vol).

Molar Yield: 75-81% (56 gm)
Chemical Purity: 95-97% (as measured by HPLC)

Sitagliptin Free Base (01)

Boc-protected sitagliptin (22.0 gm, 0.043 mol) (12) was taken in methanol (10 vol, 220.0 ml). The suspension was stirred for 15 minutes to give a partially clear solution. To the partially clear solution, 25% methanolic hydrochloride solution (1.0 vol, 22.0 ml) was added at 25-30° C. The reaction mixture was stirred for 10 hours at 25-30° C. After stirring for 10 hours at 25-30° C., the reaction mixtures was warmed up to 40-45° C. for 2 hours. The methanol was distilled out completely at 40-45° C. under reduce pressure to give a white gummy residue. The gummy residue was basified by using 10% sodium carbonate (10.0 vol, 220.0 ml) and sitagliptin free base (01) was extracted in ethyl acetate (3×10.0 vol, 3×220.0 ml). The combined ethyl acetate layers were washed with water (3×10 vol, 3×220.0 ml) and distilled out completely at 40-45° C. under reduced pressure to give gummy brown coloured oil. The oil was further purified by an acid base purification method using H$_3$PO$_4$ to give a free flowing off-white coloured solid. The off-white coloured solid was further crystallised from toluene (20.0 vol, 440.0 ml) to give pure sitagliptin free base (01).

Molar Yield: 80-85% (15.0 gm)
Chemical Purity: 97-99% (as measured by HPLC)
Enantiomeric Purity: 99.85-100% (as measured by chiral HPLC)

Salts of sitagliptin free base (01) can be readily prepared using known methods disclosed in the prior art which are included herein by reference.

It will be understood that the present invention has been described above by way of example only. The examples are not intended to limit the scope of the invention. Various modifications and embodiments can be made without departing from the scope and spirit of the invention, which is defined by the following claims only.

The invention claimed is:

1. A process for the preparation of enantiomerically enriched sitagliptin, or a pharmaceutically acceptable salt thereof, comprising the steps:
   (i) resolving a racemic β-amino acid, or a derivative thereof, with an acid resolving agent to form an enantiomerically enriched β-amino acid or a derivative thereof;
   (ii) reacting the enantiomerically enriched β-amino acid or derivative thereof with 3-trifluoromethyl-5,6,7,8-tetrahydro[1,2,4]triazolo[4,3-a]pyrazine or a salt thereof; and
   (iii) isolating enantiomerically enriched sitagliptin;
   wherein the derivative is an alkyl, alkenyl, alkynyl, aryl or arylalkyl ester.

2. A process according to claim 1, wherein the β-amino acid derivative is
   a C1 to C6 alkyl ester or a benzyl ester or substituted benzyl ester.

3. A process according to claim 1, wherein the β-amino acid is
   3-amino-4-(2,4,5-trifluorophenyl)butanoic acid or a derivative thereof,
   wherein the derivative is an alkyl, alkenyl, alkynyl, aryl or arylalkyl ester.

4. A process according to claim 1, wherein the acid resolving agent is
   an enantiomer of mandelic acid, tartaric acid, camphor-10-sulphonic acid, camphor-3-sulphonic acid, 3-bromo-camphor-9-sulphonic acid, 2-keto-gulonic acid, α-methoxyphenylacetic acid, 2-nitrotartranilic acid, malic acid, 2-phenoxypropionic acid, N-acetylleucine, N-(α-methylbenzyl)succinamic acid, N-(α-methylbenzyl)phthalamic acid, quinic acid, di-O-isopropylidene-2-oxo-L-gulonic acid, 2-hydroxy-4-isopropenyl-1-methyl-cyclohexane-1-sulphonic acid, O,O'-di-p-toluoyl-(L)-tartaric acid, O,O'-dibenzoyl-(L)-tartaric acid, (R)-3-chloro-mandelic acid, or (R)-3-bromo-mandelic acid.

5. A process according to claim 1, comprising the steps of:
   (a) treating a racemic β-amino acid, or a derivative thereof, with an acid resolving agent, to obtain an enantiomerically enriched salt;
   (b) optionally crystallising the enantiomerically enriched salt; and
   (c) dissolving or suspending the enantiomerically enriched salt obtained in step (a) or (b) in an organic solvent or water or a mixture thereof, and adjusting the pH of the solution or suspension with a base to obtain an enantiomerically enriched β-amino acid or a derivative thereof, wherein the derivative is an alkyl, alkenyl, alkynyl, aryl or arylalkyl ester.

6. A process according to claim 5, wherein:
(i) the base used in step (c) is selected from an organic base, an inorganic base or a mixture thereof; and
(ii) step (a) is carried out in an organic solvent, optionally in the presence of water.

7. A process according to claim 1, wherein the salt of sitagliptin is the dihydrogen phosphate salt.

8. A process according to claim 4, wherein the enantiomer of mandelic acid is (R)-(−)-mandelic acid or (S)-(+)-mandelic acid.

9. A process according to claim 5, wherein the acid resolving agent is (R)-(−)-mandelic acid.

10. A process according to claim 1, wherein the β-amino acid derivative is a C1 to C6 alkyl ester.

11. A process according to claim 1, wherein the β-amino acid derivative is a methyl or ethyl ester.

12. A process according to claim 1, wherein the β-amino acid is methyl 3-amino-4-(2,4,5-trifluorophenyl)butanoate.

13. A process according to claim 6, wherein the base used in step (c) is an organic base, wherein the organic base is an amine selected from methylamine, dimethylamine, trimethylamine, ethylamine, diethylamine, triethylamine, N,N-diisopropylethylamine, cyclohexylamine, or a mixture thereof.

14. A process according to claim 6, wherein the base used in step (c) is an inorganic base, wherein the inorganic base is ammonia, a metal hydroxide, a metal carbonate, or a mixture thereof, wherein the metal hydroxide is sodium hydroxide, potassium hydroxide or lithium hydroxide, and/or wherein the metal carbonate is sodium carbonate, lithium carbonate or calcium carbonate.

15. A process according to claim 6, wherein step (a) is carried out in an organic solvent, optionally in the presence of water, wherein the organic solvent is an alcohol, a ketone, an ether, an alkane, a cycloalkane, a formamide, an acetate, a halogenated solvent or a mixture thereof.

16. A process according to claim 6, wherein step (a) is carried out in an organic solvent, optionally in the presence of water, wherein the organic solvent is selected from methanol, ethanol, n-propanol, isopropanol, n-butanol, i-butanol, t-butanol, 2-pentanol, 3-pentanol, 4-penten-2-ol, 1,6-hexanediol, 1-hexanol, 5-hexen-1-ol, glycerol, 1-heptanol, 2-heptanol, 1-octanol, 2-octanol, 3-octanol or a mixture thereof.

\* \* \* \* \*